United States Patent
Leuthardt et al.

(10) Patent No.: US 10,709,321 B2
(45) Date of Patent: Jul. 14, 2020

(54) SELF-CLEANING ENDOSCOPE

(71) Applicant: WASHINGTON UNIVERSITY, St. Louis, MO (US)

(72) Inventors: Eric C. Leuthardt, St. Louis, MO (US); Guy Genin, St. Louis, MO (US); Chester Yarbrough, St. Louis, MO (US); Thane Somers, St. Louis, MO (US); Daniel Margolis, St. Louis, MO (US)

(73) Assignee: Washington University, St. Louis, MO (US)

( * ) Notice: Subject to any disclaimer, the term of this patent is extended or adjusted under 35 U.S.C. 154(b) by 364 days.

(21) Appl. No.: 15/647,700

(22) Filed: Jul. 12, 2017

(65) Prior Publication Data

US 2018/0014720 A1    Jan. 18, 2018

Related U.S. Application Data

(60) Provisional application No. 62/361,753, filed on Jul. 13, 2016.

(51) Int. Cl.
*A61B 1/12* (2006.01)
*A61B 1/00* (2006.01)
*A61B 90/70* (2016.01)

(52) U.S. Cl.
CPC .......... *A61B 1/122* (2013.01); *A61B 1/00091* (2013.01); *A61B 1/00119* (2013.01);
(Continued)

(58) Field of Classification Search
CPC ............ A61B 1/00091; A61B 1/00096; A61B 1/00119; A61B 1/122; A61B 1/126; A61B 90/70; A61B 1/00142
(Continued)

(56) References Cited

U.S. PATENT DOCUMENTS 1,153,945 A * 9/1915 Mustin ................. B60R 1/0602
                                                                359/508
2,298,063 A * 10/1942 MacPherson .......... G02B 23/16
                                                                359/508
(Continued)

FOREIGN PATENT DOCUMENTS

GB        2198256 A       6/1988
JP     2007105314 A       4/2007
(Continued)

OTHER PUBLICATIONS

Reynolds W., Jr. The first laparoscopic cholecystectomy. JSLS. 2001;5(1):89-94.
(Continued)

*Primary Examiner* — Aaron B Fairchild
(74) *Attorney, Agent, or Firm* — Armstrong Teasdale LLP (57) ABSTRACT

A self-cleaning endoscope and methods of using the same are described. The self-cleaning endoscope includes a housing having a distal end and a proximal end opposite the distal end, a lens positioned at the distal end of the housing, and a lens protector coupled to the distal end of the housing external to the lens. The self-cleaning endoscope also includes a shaft extending longitudinally through the housing. The shaft is operatively coupled to the lens protector and configured to rotate the lens protector about an axis of rotation coaxial with the shaft. The self-cleaning endoscope further includes a motor at the proximal end of the housing. The motor is operatively coupled to the shaft and configured to drive rotation of the shaft.

17 Claims, 8 Drawing Sheets

(52) U.S. Cl.
CPC .............. *A61B 1/126* (2013.01); *A61B 90/70* (2016.02); *A61B 1/00096* (2013.01); *A61B 2090/701* (2016.02)

(58) Field of Classification Search
USPC ........................................ 600/127, 129, 175
See application file for complete search history.

(56) References Cited

U.S. PATENT DOCUMENTS

| | | | |
|---|---|---|---|
| 3,145,249 A | 8/1964 | Meltzer | |
| 3,859,987 A * | 1/1975 | Holstad | A61B 1/253 600/247 |
| 4,408,991 A * | 10/1983 | Engel | A61B 1/253 433/30 |
| 4,919,113 A | 4/1990 | Sakamoto et al. | |
| 5,225,001 A | 7/1993 | Manni et al. | |
| 5,313,934 A | 5/1994 | Wiita et al. | |
| 5,315,333 A | 5/1994 | Nash | |
| 5,382,297 A | 1/1995 | Valentine et al. | |
| 5,392,766 A | 2/1995 | Masterson et al. | |
| 5,400,767 A | 3/1995 | Murdoch | |
| 5,419,311 A * | 5/1995 | Yabe | A61B 1/00091 600/124 |
| 5,464,008 A | 11/1995 | Kim | |
| 5,514,084 A | 5/1996 | Fisher | |
| 5,518,502 A | 5/1996 | Kaplan et al. | |
| 5,575,756 A | 11/1996 | Karasawa et al. | |
| 5,654,824 A * | 8/1997 | Tarr | A61B 1/126 359/872 |
| 6,126,592 A | 10/2000 | Proch et al. | |
| 6,193,731 B1 | 2/2001 | Oppelt et al. | |
| 6,354,992 B1 | 3/2002 | Kato | |
| 6,409,657 B1 | 6/2002 | Kawano | |
| 6,447,446 B1 | 9/2002 | Smith et al. | |
| 6,607,606 B2 | 8/2003 | Bronson | |
| 6,638,214 B2 | 10/2003 | Akiba | |
| 6,712,757 B2 | 3/2004 | Becker et al. | |
| 6,755,782 B2 | 6/2004 | Ogawa | |
| 6,923,759 B2 | 8/2005 | Kasahara et al. | |
| 6,996,338 B2 | 2/2006 | Sherwin | |
| 7,104,657 B2 | 9/2006 | Sherwin | |
| 7,341,556 B2 | 3/2008 | Shalman | |
| 7,959,561 B2 | 6/2011 | Akui et al. | |
| 8,001,984 B2 | 8/2011 | Sasaki | |
| 8,047,215 B1 | 11/2011 | Sasaki | |
| 8,079,952 B2 | 12/2011 | Fujimoto | |
| 8,397,335 B2 | 3/2013 | Gordin et al. | |
| 2003/0137752 A1 * | 7/2003 | Sherwin | A61B 1/126 359/809 |
| 2006/0258913 A1 | 11/2006 | Jerjomin | |
| 2006/0293559 A1 | 12/2006 | Grice et al. | |
| 2008/0200764 A1 * | 8/2008 | Okada | A61B 1/00068 600/157 |
| 2009/0240111 A1 | 9/2009 | Kessler et al. | |
| 2009/0264703 A1 | 10/2009 | Pribanic | |
| 2010/0168520 A1 | 7/2010 | Poll et al. | |
| 2010/0174144 A1 | 7/2010 | Hsu et al. | |
| 2012/0022331 A1 | 1/2012 | Poll et al. | |
| 2012/0101338 A1 | 4/2012 | O'Prey et al. | |
| 2012/0108904 A1 | 5/2012 | Ma et al. | |
| 2012/0178995 A1 | 7/2012 | Newton, IV | |
| 2012/0184897 A1 | 7/2012 | Poll | |
| 2012/0238818 A1 | 9/2012 | O'Prey et al. | |
| 2013/0197311 A1 | 8/2013 | Sherwin | |
| 2015/0282695 A1 * | 10/2015 | Tay | A61B 1/00135 600/124 |
| 2015/0286295 A1 | 10/2015 | Pepe | |

FOREIGN PATENT DOCUMENTS

| | | |
|---|---|---|
| JP | 2008279202 A | 11/2008 |
| JP | 2010022758 A | 2/2010 |
| JP | 4756986 B2 | 8/2011 |
| WO | 2008097294 A1 | 8/2008 |
| WO | 2011128894 A1 | 10/2011 |

OTHER PUBLICATIONS

Garabrant M, Klein R, Tsui C. Minimally invasive surgery: National trends in adoption and future directions for hospital strategy. Surgical Endoscopy. Jul. 2013;27(7):2253-7.

Sutton E, Youssef Y, Meenaghan N, Godinez C, Xiao Y, Lee T, Dexter D, Park A. Gaze disruptions experienced by the aparoscopic operating surgeon. Surg Endosc. 2010;24:1240-1244. doi: 10.1007/s00464-009-0753-3.

* cited by examiner

SELF-CLEANING ENDOSCOPE

CROSS-REFERENCE TO RELATED APPLICATION

This application claims priority to U.S. Provisional Patent Application No. 62/361,753 entitled SELF-CLEANING ENDOSCOPE filed Jul. 13, 2016, which is hereby incorporated by reference in its entirety.

BACKGROUND

The field of this disclosure relates generally to surgical tools and, more particularly, to a self-cleaning endoscope used for surgeries.

Endoscopes are long slender tools used for minimally invasive surgery. A tip at one end of the endoscope contains a camera and fiber optic lights, covered by one or more lenses. In operation, this end of the endoscope can be inserted into an incision in a patient through a trocar. The other end of the endoscope includes a camera output and, in at least some cases, a handle. The camera feeds an internal image of the patient to a surgeon through either an eyepiece or a monitor. Typically, surgeries using an endoscope are considered "minimally invasive". For example, a traditional appendectomy would require an inch or two incision. However, endoscopic surgery has reduced incision size to about ten millimeters or smaller. Often, a diameter of the tip of the endoscope is ten millimeters or less. Smaller diameter endoscopes may be required for child surgeries and/or surgeries in sensitive areas, such as the brain, or small areas, such as the knee or shoulder. Endoscopes for these surgeries, for example, may have a diameter less than five millimeters.

Frequently during endoscopic surgery, the lens covering the camera and/or lights becomes obscured with condensate, blood, and/or other debris. As a result, the surgeon may need to remove the endoscope from the patient to wipe the lens, as a dirty lens causes the surgeon to operate with obscured vision. Removing the endoscope to clean the lens distracts the surgeon, delays the surgery, and/or increases the time the patient is under anesthesia.

Providing the surgeon with the ability to clean the lens without removing the endoscope would allow the surgeon to maintain focus and perform quicker procedures, which may thereby lower hospital costs and/or decrease patient time under anesthesia.

As a result, there is a need for an endoscope capable of cleaning its lens in vivo.

BRIEF DESCRIPTION

In one aspect, a self-cleaning endoscope generally comprises a housing having a distal end and a proximal end opposite the distal end, a lens positioned at the distal end of the housing, and a lens protector coupled to the distal end of the housing external to the lens. The self-cleaning endoscope also includes a shaft extending longitudinally through the housing, the shaft operatively coupled to the lens protector and configured to rotate the lens protector about an axis of rotation coaxial with the shaft. The self-cleaning endoscope further includes a motor at the proximal end of the housing, the motor operatively coupled to the shaft and configured to drive rotation of the shaft.

In another aspect, a self-cleaning endoscope generally comprises a housing having a distal end and a proximal end opposite the distal end, a lens protector coupled to the distal end of the housing, and a motor at the proximal end of the housing. The self-cleaning endoscope also includes a shaft extending from the motor through the lens protector. The shaft is operatively coupled to the motor such that activation of the motor causes rotation of the shaft about an axis of rotation, and the shaft is operatively coupled to the lens protector and configured to rotate the lens protector about the axis of rotation. The self-cleaning endoscope also includes a fluid source in fluid communication with the shaft and configured to drive fluid through the shaft to an external surface of the lens protector.

In yet another aspect, s method of using a self-cleaning endoscope is provided. The method includes inserting a distal end of the endoscope into a viewing location of a patient, the distal end including a lens and a lens protector external to the lens. The method also includes actuating a trigger located on a handle at a proximal end of the endoscope, the actuating causing activation of a motor at the proximal end of the endoscope to rotate a shaft coupled to the motor, wherein the shaft is operatively coupled to the lens protector such that rotation of the shaft causes rotation of the lens protector.

In a further aspect, a self-cleaning endoscope is provided. The endoscope includes a tube having a distal end and a proximal end opposite the distal end, a lens located at the distal end of the tube, a handle located at the proximal end of the tube, and a cleaning assembly. The cleaning assembly includes a ratchet mechanism coupled to the tube and a cleaning ribbon operatively connected to the ratchet mechanism across the lens. The cleaning ribbon includes a plurality of holes therein and segmenting elements arranged between adjacent holes of the plurality of holes. The segmenting elements are configured to inhibit wicking of moisture past the segmenting elements. The ratchet mechanism is configured to draw the cleaning ribbon across the lens. Each of the holes of the plurality of holes is sized and shaped to be positioned over the lens.

DETAILED DESCRIPTION OF THE DRAWINGS

The exemplary systems, apparatus, and methods described herein overcome at least some known disadvantages associated with at least some known surgical tools, specifically endoscopes. More particularly, the embodiments described herein include a self-cleaning endoscope configured to help maintain visibility through an endoscope lens without withdrawing the endoscope from a viewing region within a patient's body. In a first embodiment, the endoscope includes a housing having a distal end and a proximal end. A lens protector coupled to the distal end of the housing is external to and spaced from an endoscope lens. The endoscope further includes a shaft extending longitudinally through the housing. The shaft is operatively coupled to the lens protector and configured to rotate the lens protector about an axis of rotation coaxial with the shaft. The endoscope also includes a motor at the proximal end of the housing. The motor is operatively coupled to the shaft and is configured to drive rotation of the shaft, which rotates the lens protector therewith. In this way, any debris on the lens protector can be thrown off by the centrifugal force generated by the rotation of the lens protector. Housing the motor at the proximal end of the housing, or at a "base" or handle of the endoscope, enables a weight of the distal end of the endoscope to be light and, accordingly, more easily maneuverable. In some cases, the shaft extends through the lens protector. The shaft is in fluid communication with a fluid source configured to drive fluid through the shaft to an external surface of the lens protector. The fluid saturates condensate and/or small debris to help throw the condensate and/or small debris from the lens protector.

In a second embodiment, the endoscope includes a tube having including a distal end and a proximal end opposite the distal end, a lens located at the distal end of the tube, a handle located at the proximal end of the tube, and a cleaning assembly. The cleaning assembly can be an "add on" or "retrofit" to any existing endoscope or can be part of a new endoscope. The cleaning assembly includes a ratchet mechanism coupled to the endoscope tube. A cleaning ribbon is operatively connected to the ratchet mechanism across the lens. The cleaning ribbon includes a plurality of holes. The ratchet mechanism draws the cleaning ribbon across the lens until a first hole of the plurality of holes is positioned over the lens. The action of drawing the cleaning ribbon over the lens wipes away any debris or condensate on the lens. Moreover, the cleaning ribbon includes segmenting elements arranged between each hole in the cleaning ribbon. The segmenting elements are configured to inhibit the wicking of any moisture therepast. Accordingly, any moisture wicked by the cleaning ribbon while cleaning the lens does not extend substantially into a "clean" side of the cleaning ribbon.

Figure 1:
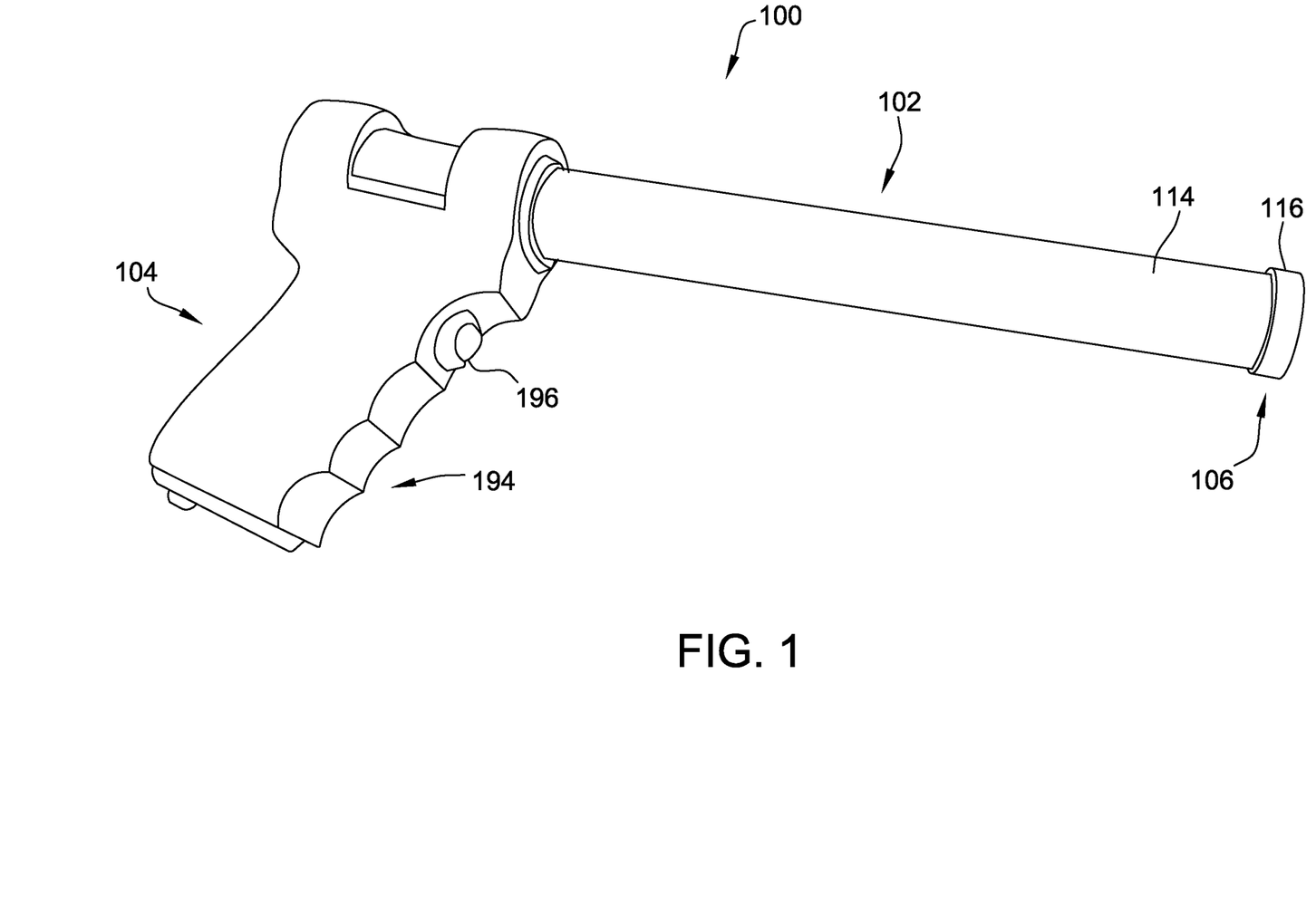
FIG. 1 is perspective view of one embodiment of a self-cleaning endoscope.
Figure 2:
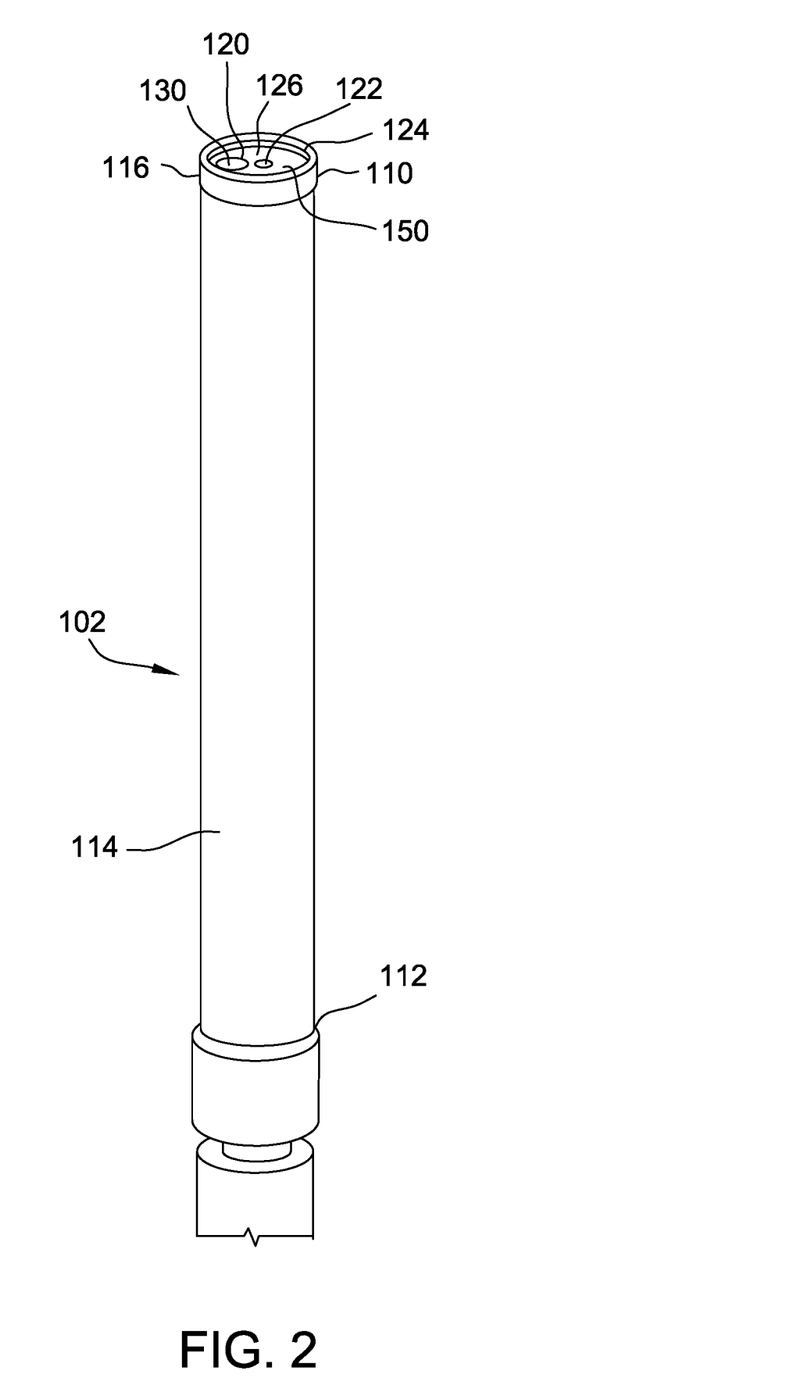
FIG. 2 is an enlarged view of a housing of the self-cleaning endoscope shown in FIG. 1.
Figure 3:
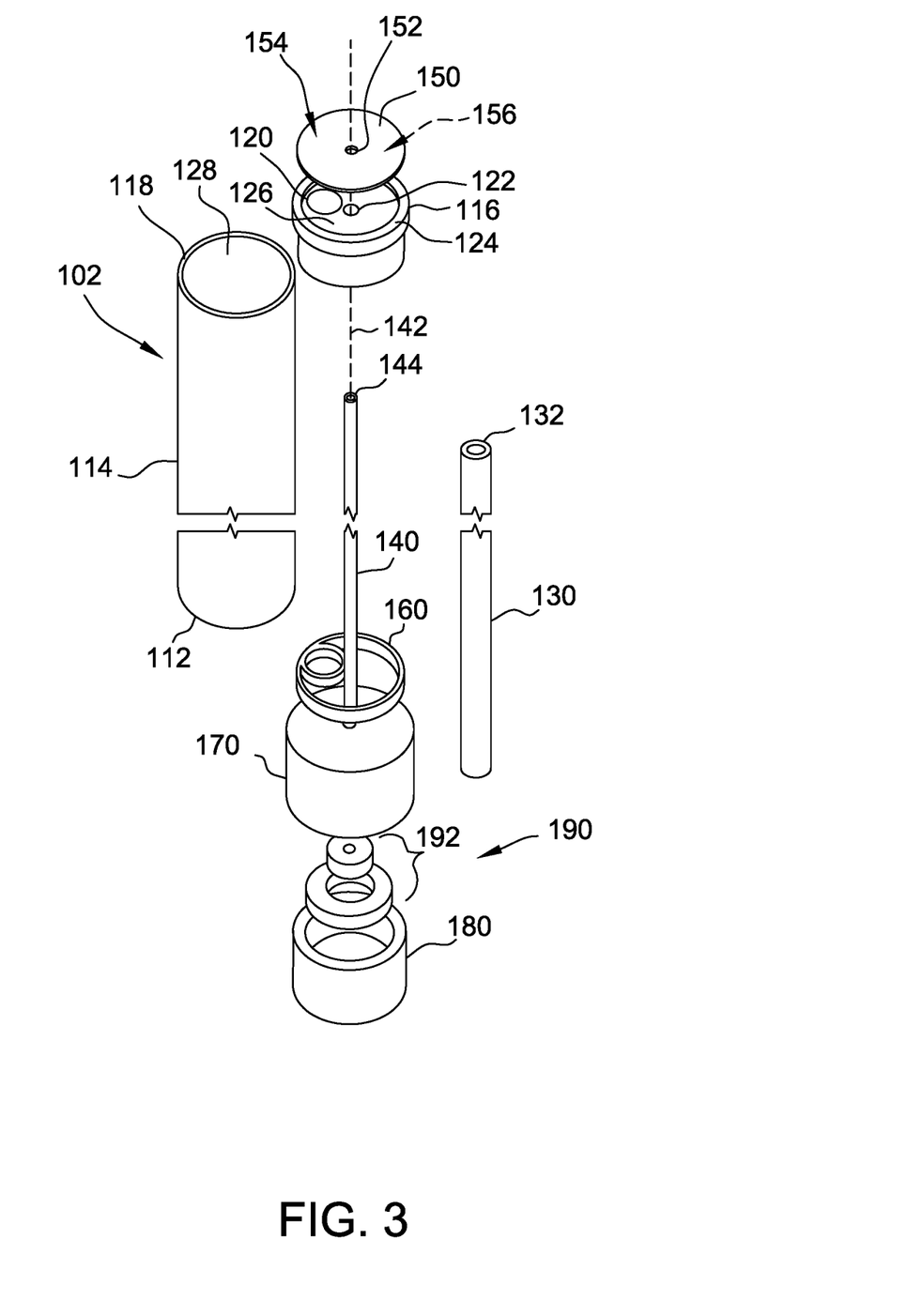
FIG. 3 is an exploded view of the housing shown in FIG. 2.
Figure 4:
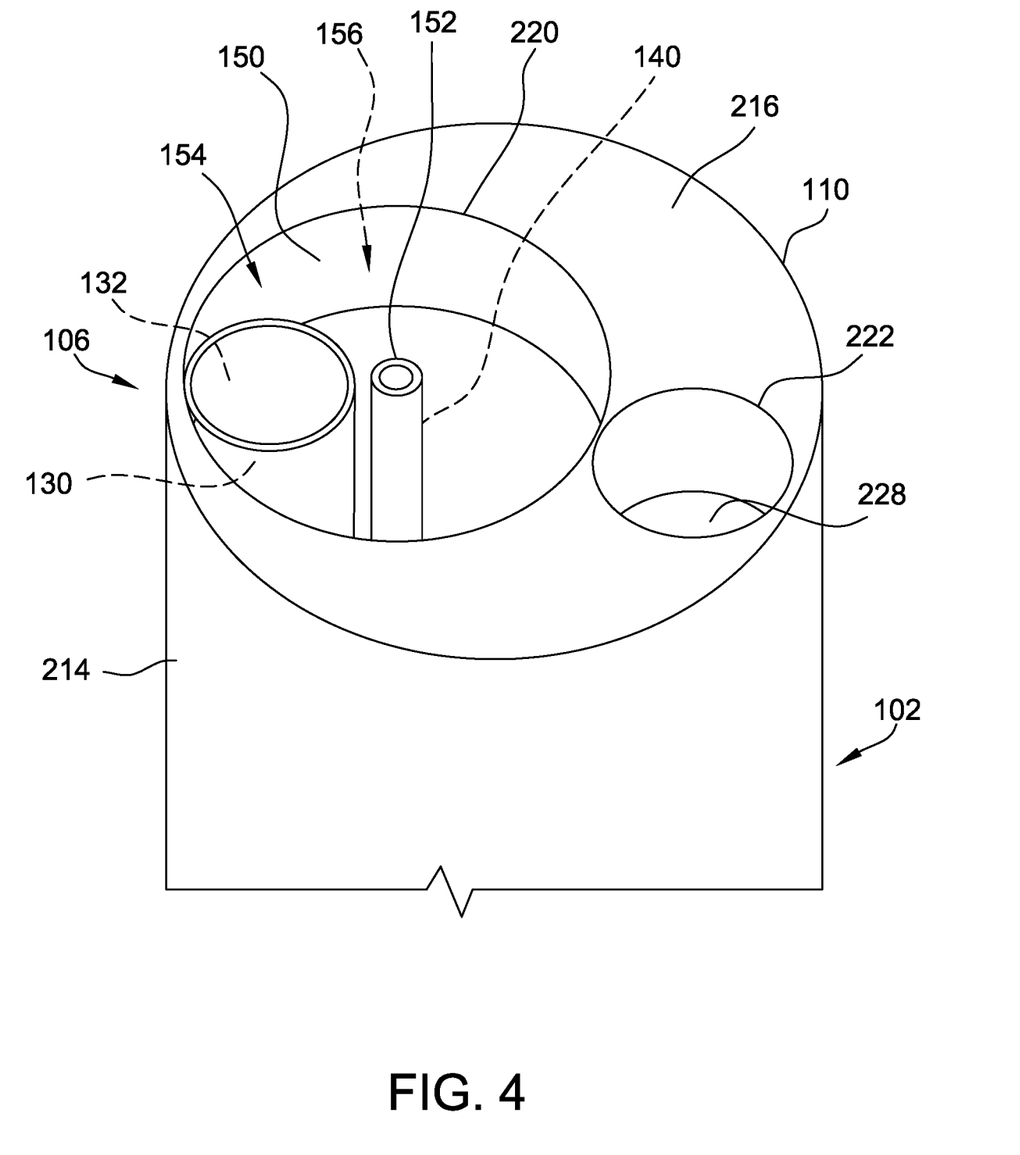
FIG. 4 is an enlarged view of one embodiment of a tip of housing shown in FIG. 2.

Turning now to the figures, FIG. 1 is perspective view of one embodiment of a self-cleaning endoscope 100, FIG. 2 is an enlarged view of a housing 102 of the self-cleaning endoscope 100, and FIG. 3 is an exploded view of the housing 102. FIG. 4 is an enlarged view of a tip 106 of one embodiment of the self-cleaning endoscope 100. The endoscope 100 includes, in general, a housing 102 and a handle 104. The housing 102 is configured for insertion into a viewing region (not shown) of a patient (not shown) through an incision in the patient during an endoscopic surgery, for example, laparoscopic surgery. The housing 102 may be sized and shaped (e.g., in diameter and/or length) according to various standards. In the illustrated embodiment, the housing 102 is substantially cylindrical in shape. In alternative embodiments, the housing 102 can have any other suitable shape. The housing 102 may be rigid, flexible, and/or semi-rigid, without departing from the scope of the disclosure. Suitably, the housing 102 is fabricated from a material that is sterilizable and suitable for surgical purposes, such stainless steel.

As illustrated in FIGS. 2 and 3, the housing 102 includes a distal end 110 and an opposing proximal end 112. Generally, the distal end 110 of the housing 102 corresponds to a distal end or tip 106 of the endoscope 100. The housing 102 (FIG. 1) is coupled to the handle 104 at the proximal end 112. In one embodiment, as shown in FIGS. 1-3, the housing 102 includes a tube 114 that is open at both ends, and a cap 116. The tube 114 is configured to receive the cap 116 at the distal end 118 of the tube 114. In some embodiments, the cap 116 is fabricated from the same material as the tube 114 (e.g., stainless steel). In other embodiments, the cap 116 is fabricated from a different material (e.g., plastic). The cap 116, as shown in FIGS. 2 and 3, defines at least two openings, specifically a first opening 120 and a second opening 122. The first opening 120 is sized and shaped to receive an optical component 130, which is contained within the housing 102 (e.g., within the tube 114). The optical component 130 includes any elements necessary to provide visual feedback to an operator of the endoscope 100, including a camera, wires, fibers, lights, feeds, and/or other elements. The optical component 130 includes a lens 132. The lens 132 is positioned within the first opening 120, such that an environment around the endoscope tip 106 can be viewed by the endoscope operator. The second opening 122, which is centrally located within the cap 116, is sized and shaped to receive a shaft 140 therethrough, as described further herein. In the illustrated embodiment, the cap 116 also defines a ridge 124 that is raised with respect to a top face 126 of the cap 116. The ridge 124 is configured to receive and retain a lens protector 150 therein. The lens protector 150 is external to and spaced from the lens 132. The cap 116 and/or the lens protector 150 may include a sealing component (not shown) configured to maintain a seal between the lens protector 150 and the cap 116 when the lens protector 150 is rotated to dislodge or throw debris therefrom.

The lens protector 150 is configured to protect the lens 132 (and the entirety of the optical component 130 and an interior 128 of the housing 102) from damage and/or dirtying within the environment of the endoscope tip 106 (e.g., a viewing region within a patient), while maintaining visibility through the lens 132. The lens protector 150 is fabricated from any suitable transparent material, such as plastic or glass. In the illustrated embodiment, the lens protector 150 defines a thru-hole 152. The thru-hole 152 is sized and shaped to receive the shaft 140 therethrough, as described further herein.

In another suitable embodiment, as shown in FIG. 4, the housing 102 includes a single, integrally formed component, such a tube 214 with a closed end 216. In this embodiment, the closed end 216 defines at least one opening, specifically a first opening 220 and a second opening 222. The first opening 220 is sized and shaped to receive the lens protector 150 therein. The first opening 220 and/or the lens protector 150 may include a sealing component (not shown) configured to maintain a seal between the lens protector 150 and the first opening 220 when the lens protector 150 is rotated to throw debris therefrom. As shown, the optical component 130, including the lens 132, are also received in the first opening 220. The second opening 222 is sized and shaped to receive any additional surgical tool (not shown) therethrough, such that the second opening 222 functions as a working channel for the surgical tool. For example, the second opening 222 may receive a light, a suction device, an optical component, a cutting device, an ablation tool, and/or any other device therethrough. In some embodiments, the housing tube 214 further includes an internal tube (not shown) connected to the second opening 222, such that any debris that may enter into the tube 214 through the second opening 222 does not contaminate an entire interior 228 of the tube 214. In other components, the surgical tool may fit snugly into the second opening 222, substantially sealing the second opening 222 from the environment around the endoscope tip 106.

With reference again to FIGS. 2 and 3, the tube 114 (or the tube 214, shown in FIG. 4) encloses the shaft 140 and the optical component 130 therein, as well as a brace 160. The brace 160 is configured to maintain the position of the optical component 130 and/or the shaft 140 within the housing 102. The brace 160 is fabricated from any suitable material, such as a metal, alloy, plastic, and/or composite. The brace 160 may be positioned within the tube 114 and friction fit and/or adhered to the interior surface 128 of the tube 114.

In some embodiments, a motor 170 is also contained within the tube 114 (or the tube 214). In other embodiments, the motor 170 is not housed within the tube 114 but rather is housed in the handle 104, adjacent to the proximal end 112 of the tube 114. The motor 170 is operatively coupled to the shaft 140, and is configured to cause rotation of the shaft 140 about an axis of rotation 142. The motor 170 may include any suitable kind of motor, including an electric motor.

The shaft 140 extends from the motor 170, through the housing 102 to the lens protector 150. In the illustrated embodiment, a distal end 144 of the shaft 140 is co-planar with an external surface 154 of the lens protector 150. In an alternative embodiment, the distal end 144 of the shaft 140 is other than co-planar with the external surface 154 of the lens protector 150. For example, in certain embodiments, the shaft 140 may only extend to an interior surface 156 of the lens protector 150. Moreover, in some embodiments, the distal end 144 of the shaft 140 is received in the thru-hole 152 of the lens protector 150 in such a way as to snugly couple the shaft 140 to the lens protector 150, for example, via a friction fit and/or using an adhesive or sealant (not shown). The shaft 140 is fabricated from any suitable material, including a metal, alloy, plastic, and/or composite material. In the illustrated embodiment, the shaft 140 is a tube with open ends. In other embodiments, the shaft 140 is a solid (i.e., not hollow) rod.

In the illustrated embodiment, the endoscope 100 further includes a fluid source 180. The fluid source 180 is any suitable container for containing a fluid. In the illustrated embodiment, the fluid source 180 is in fluid communication with the shaft 140, such that fluid from the fluid source 180 may be channeled through the shaft 140. More particularly, the fluid source 180 channels fluid through the shaft 140 to the external surface 154 of the lens protector 150. During endoscopic surgeries, condensate and small drops of debris may not have enough mass to be thrown from the lens protector 150. By channeling the fluid to the external surface 154 of the lens protector 150, the cohesion of the fluid saturates the condensate or small debris, giving it enough mass to be spun away from the lens protector 150. The fluid source 180 contains water, saline, and/or any other fluid suitable to draw up debris from the external surface 154 of the lens protector 150. The fluid source 180 may channel the fluid in any suitable amount, for example, about 0.1 mL to about 1 mL, or about 0.25 mL to about 0.75 mL, or about 0.5 mL. In some embodiments, the fluid source 180 is housed within the tube 114 (or the tube 214). In other embodiments, the fluid source 180 is not enclosed within the tube 114 but rather is contained within the handle 104 adjacent to the proximal end 112 of the tube 114. In still other embodiments, the fluid source 180 may be external to both the housing 102 and the handle 104. In these embodiments, the fluid source 180 may be coupled to the shaft 140 via a conduit (not shown), such as tubing.

In the example embodiment, the endoscope 100 also includes a bearing assembly 190 that provides a bearing interface between the fluid source 180 and the shaft 140. This bearing interface permits rotation of the shaft 140 while maintaining the fluid source 180 in a stationary position. In the illustrated embodiment of FIG. 3, the bearing assembly 190 includes one stationary-to-rotating bearing 192. The bearing 192 may include, for example, a plain bearing, a rolling-element bearing, a fluid bearing, a magnetic bearing, and/or any other suitable bearing configuration. In other embodiments, the bearing assembly 190 includes a more complex assembly of various bearings.

In the illustrated embodiment, the shaft 140 functions not only as a channel for the fluid from the fluid source 180 but as a drive shaft to drive rotation of the lens protector 150. In some embodiments, the shaft 140 may drive rotation of the entire housing 102, including the lens protector 150. In these embodiments, the shaft 140 is coaxial with the housing 102 (e.g., the tube 114/214). In other embodiments, the shaft 140 may drive rotation only of the lens protector 150. In such embodiments, the shaft 140 may be coaxial with the housing 102 and/or other than coaxial with the housing 102.

As seen in FIG. 1, the handle 104 of the endoscope 100 is coupled to the proximal end 112 of the housing 102. The handle 104 is fabricated from a rigid and/or semi-rigid material, such as plastic, composite, metal, and/or alloy material. In some embodiments, the handle 104 includes a molded grip 194, which may be integrally formed with a body of the handle 104 and/or formed as a separate component and coupled to the body of the handle 104. The handle 104 further includes a trigger 196. The trigger 196 includes at least one trigger component. In one embodiment, the trigger 196 includes a first trigger component and a second trigger component. The first trigger component is operatively coupled to the motor 170, such that actuation of the first trigger component activates the motor 170 to drive rotation of the shaft 140 and, thus, the lens protector 150. The second trigger component is operatively coupled to the fluid source 180, such that actuation of the second trigger component activates the fluid source 180 to channel the fluid through the shaft 140 to the external surface 154 of the lens protector 150. In another embodiment, the trigger 196 includes only one trigger component. The single trigger component is operatively coupled to the motor 170 and the fluid source 180, such that actuation of the single trigger component activates both the motor 170 and the fluid source 180. Additionally or alternatively, the single trigger component may include a plurality of states, such that actuation of the trigger component into a first state activates the motor 170, and actuation of the trigger component into a second state activates the fluid source 180. The trigger 196 and/or components thereof may include any kind of actuatable device, such as a button, a switch, a lever, and/or any other suitable trigger.

Figure 5:
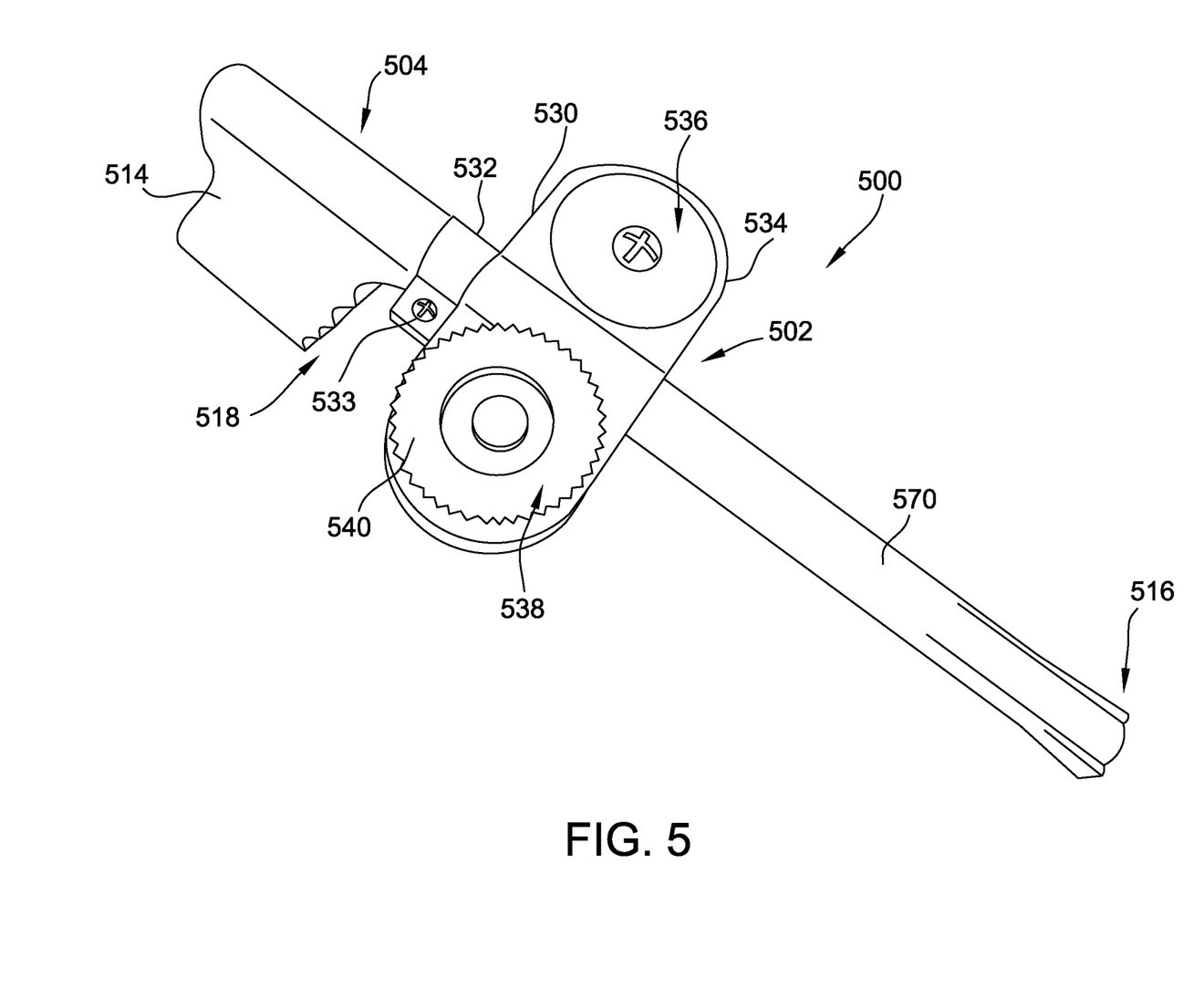
FIG. 5 is a perspective view of another embodiment of a self-cleaning endoscope.
Figure 6:
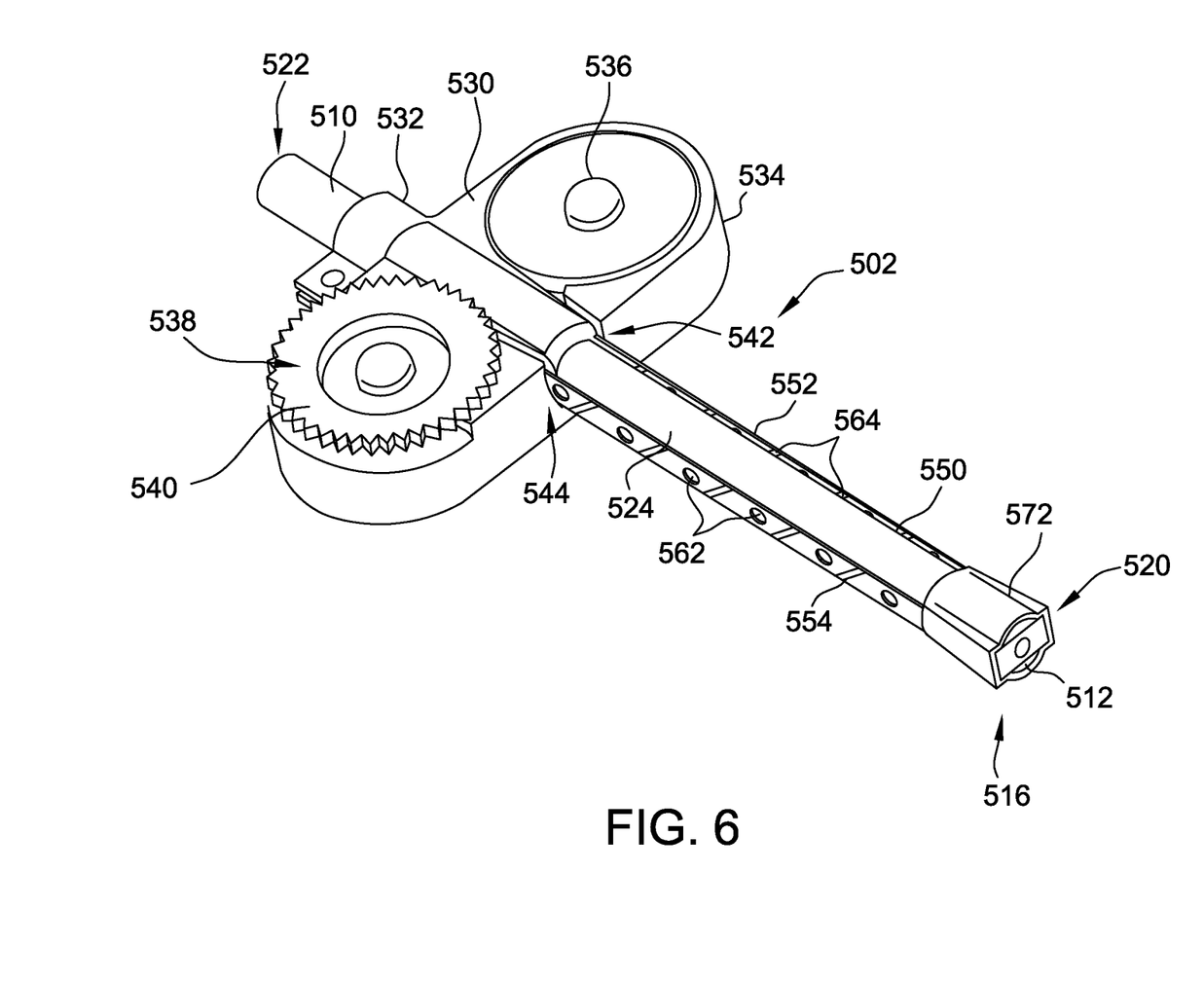
FIG. 6 is an enlarged cut-away view of the self-cleaning endoscope shown in FIG. 5.
Figure 7:
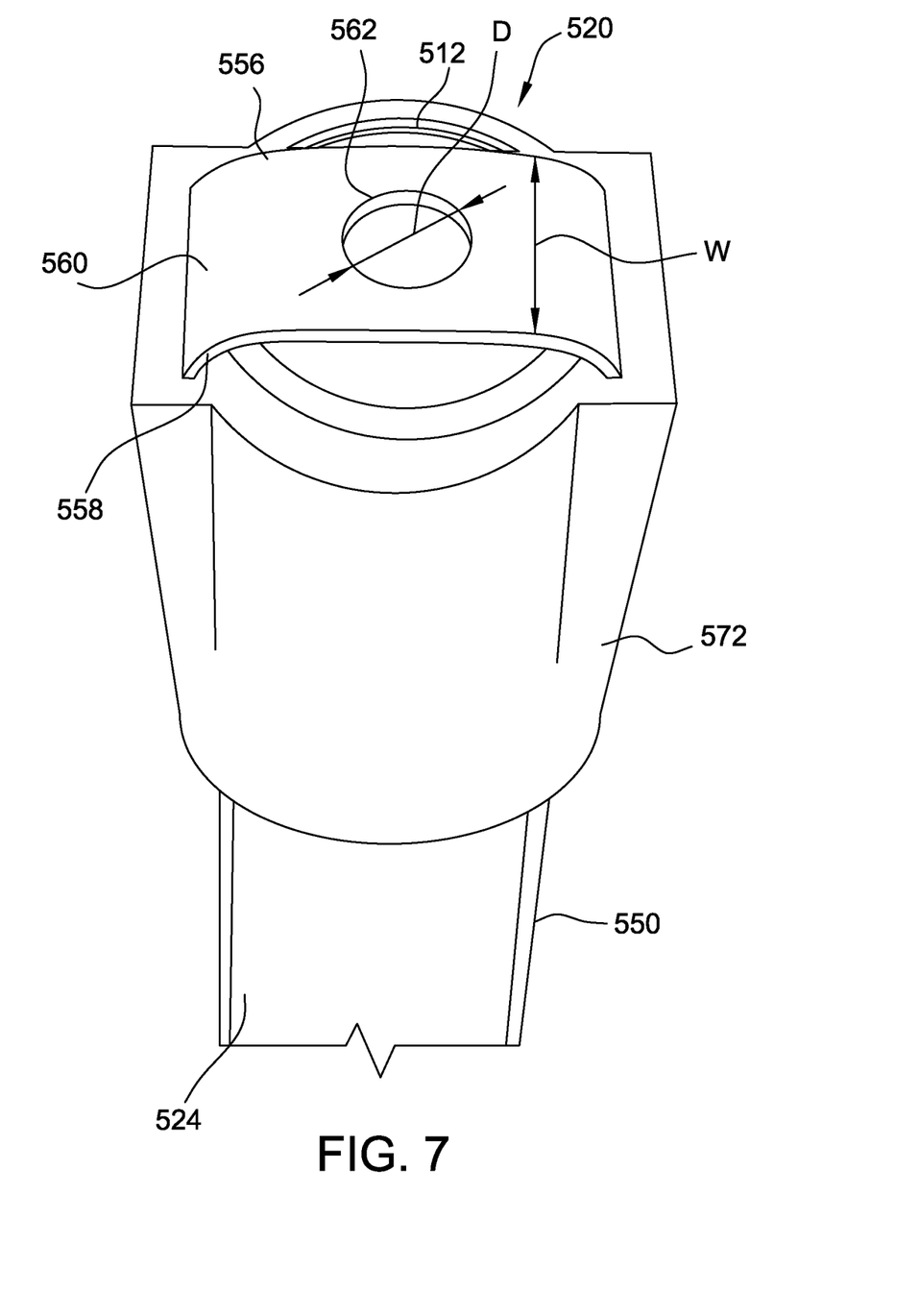
FIG. 7 is an enlarged view of a tip of the self-cleaning endoscope shown in FIG. 5.

Turning now to FIGS. 5-7, a second embodiment of a self-cleaning endoscope 500 is illustrated. More particularly, FIG. 5 is a perspective view of the self-cleaning endoscope 500, FIG. 6 is an enlarged cut-away view of the self-cleaning endoscope 500, and FIG. 7 is an enlarged view of a tip 516 of the self-cleaning endoscope 500. In this embodiment, the self-cleaning endoscope 500 is provided with an add-on or retrofit cleaning assembly 502. It is understood, however, that the self-cleaning endoscope 500 can be part of a new endoscope. The self-cleaning endoscope 500 may include any standard "standalone" or "base" endoscope 504, to which the cleaning assembly 502 is coupled to form the self-cleaning endoscope 500. Accordingly, the self-cleaning endoscope 500 should be understood to incorporate all features of both the cleaning assembly 502 and the base endoscope 504.

More specifically, the base endoscope 504 includes a tube 510, a lens 512, and a handle 514. The tube 510 includes a distal end 520 and an opposing proximal end 522, as well as a body 524 that extends between the distal end 520 and the proximal end 522. The lens 512 is coupled to the distal end 520 of the tube 510. The distal end 520 of the tube 510 generally corresponds to a distal end or tip 516 of the base endoscope 504, which is also the tip 516 of the self-cleaning endoscope 500. The tube 510 houses any necessary optical components (not shown) necessary to provide visual feedback to an operator (not shown) of the base endoscope 504, including a camera, wires, fibers, lights, feeds, and/or other elements. The handle 514 of the base endoscope 504 is coupled to the tube 510. The handle 514 is fabricated from a rigid and/or semi-rigid material, such as plastic, composite, metal, and/or alloy material. In some embodiments, the handle 514 includes a molded grip 518, which may be integrally formed with a body of the handle 514 and/or formed as a separate component and coupled to the body of the handle 514.

The cleaning assembly 502 includes a ratchet mechanism 530 and a cleaning ribbon 550. The ratchet mechanism 530 is coupled to the tube 510 along the body 524 of the tube 510. For example, the ratchet mechanism 530 may be coupled to the tube 510 along the body 524 adjacent to the handle 514. In the illustrated embodiment, the ratchet mechanism 530 includes a bracket 532 and a fastener 533 to couple the ratchet mechanism 530 (and, therefore, the cleaning assembly 502) to the tube 510. In other embodiments, the ratchet mechanism 530 includes any suitable coupling component other than and/or in addition to the bracket 532 to couple the ratchet mechanism 530 to the tube 510. The ratchet mechanism 530 can be selectively opened to move the cleaning ribbon 550 across the lens 512. For example, one end (not shown) of the cleaning ribbon 550 is drawn from one side of the ratchet mechanism 530, pulled across the lens 512, and re-inserted into another, opposing side of the ratchet mechanism 530. During operation of the self-cleaning endoscope 500, the cleaning ribbon 550 is pulled across the lens 512 to wipe away debris, moisture, condensate, etc. Accordingly, the length of the cleaning ribbon 550 that has yet to be drawn across the lens 512 may be referred to as a "clean side" 552 of the cleaning ribbon 550, and the length of the cleaning ribbon 550 that has been drawn across the lens 512 may be referred to as a "dirty side" 554 of the cleaning ribbon 550.

As shown in FIG. 5, the cleaning assembly 502 further includes a sheath 570, which may be placed over the tube 510 and the cleaning ribbon 550 to keep the cleaning ribbon 550 in place over the tube 510 and the lens 512. Moreover, the sheath 570 acts to keep the clean side 552 of the cleaning ribbon 550 clean and free of contamination before the cleaning ribbon 550 is swept across the lens 512. In some embodiments, the cleaning assembly 502 also includes a cap 572. The cap 572 is coupled to the distal end 520 of the tube 510 and further maintains the proper positioning of the cleaning ribbon 550 across the lens 512. The cap 572 and/or the sheath 570 are fabricated from any material suitable for a surgical procedure, such as a metal (e.g., stainless steel) or non-porous/sealed plastic.

In the illustrated embodiment, the ratchet mechanism 530 includes a casing 534 generally defining a spooling portion 536 and a take-up portion 538. The spooling portion 536 includes a spool (not shown) of sterile cleaning ribbon 550 inside the casing 534. The cleaning ribbon 550 is drawn out from this spool. The take-up portion 538 includes a ratchet 540. Advancing the ratchet 540 pulls the cleaning ribbon 550 across the lens 512. Moreover, the take-up portion 538 may include a one-way bearing (not shown), which, in combination with the ratchet 540, is configured to maintain tension in the cleaning ribbon 550, such that the cleaning ribbon 550 maintains contact with the lens 512 while being drawn thereacross. The take-up portion 538 may further including another spool or other take-up mechanism (not shown) within the casing 534, to collect dirtied cleaning ribbon 550. The clean side 552 of the cleaning ribbon 550 extends from an outlet 542 of the spooling portion 536 to the tip 516 of the self-cleaning endoscope 500. The dirty side 554 of the cleaning ribbon 550 extends from the tip 516 of the self-cleaning endoscope 500 to an inlet 544 of the take-up portion 538. The spooling portion 536 and the take-up portion 538 are arranged in opposition to one another across the tube 510, such that the clean side 552 of the cleaning ribbon 550 and the dirty side 554 of the cleaning ribbon 550 are also in opposition. In this way, tension in the cleaning ribbon 550 may be easily maintained. To operate the cleaning assembly 502 of the self-cleaning endoscope 500, an operator thereof need only advance the ratchet 540 of the ratchet mechanism 530 to advance the cleaning ribbon 550 from the spooling portion 536, across the lens 512, and into the take-up portion 538. In some embodiments, the self-cleaning endoscope 500 may include an alternative trigger mechanism (not shown), for example, a trigger mechanism disposed on the handle 514.

The cleaning ribbon 550 includes two opposing sides 556, 558 and a web 560 extending between the sides 556, 558. The cleaning ribbon 550 also includes a plurality of holes 562. The holes 562 are configured to permit visibility through the lens 512 after the lens 512 is cleaned by the cleaning ribbon 550, such that the cleaning ribbon 550 does not have to be moved on and off of the lens 512. Rather, the cleaning ribbon 550 can maintain taut positioning across the lens 512. An operator of the self-cleaning endoscope 500 only needs to draw the cleaning ribbon 550 across the lens 512 (into the take-up portion 538 of the ratchet mechanism 530) until a hole 562 is positioned over the lens 512.

In the example embodiment, the cleaning ribbon 550 is fabricated from an absorbent material configured to draw up or "wick" moisture from the lens 512, as well as wipe away any debris from the lens 512. Moreover, the cleaning ribbon 550 is fabricated from a material that has sufficient strength to be pulled taut over the lens 512, as well as resist fraying. In some embodiments, the sides 556, 558, and/or the web 560 of the cleaning ribbon 550 may have an elastic quality or component thereto, which may improve conformance of the cleaning ribbon 550 against the lens 512. In some embodiments, a surface of the cleaning ribbon 550 that faces the lens 512 may have a liquid-impermeable coating thereon. In this way, the cleaning ribbon 550 may wipe debris away from lens 512 without leaving excess moisture on lens 512. The cleaning ribbon 550 may be fabricated from polyester, cotton, wool, elastic, other synthetic materials, other natural materials, and/or any combination thereof. In some embodiments, the holes 562 may include a transparent material therein, such as a plastic. The holes 562 are arranged evenly, at regular intervals along the web 560 of the cleaning ribbon 550. For example, the holes 562 may be spaced about 1 mm to about 50 mm apart, about 5 mm to about 40 mm apart, about 10 mm to about 30 mm apart, or about 20 mm apart (e.g., for an 11 mm base endoscope 504; other distances between the holes 562 may be implemented for other base endoscopes 504). In alternative embodiments, the holes 562 are arranged other than evenly along the web 560 of the cleaning ribbon 550. The holes 562 have a diameter D that is chosen relative to a width W of the cleaning ribbon 550, wherein width W is taken between the sides 556, 558. The diameter D is less than the width W. The greater the width W of the cleaning ribbon 550, the greater the diameter D of the holes 562 may be. In some embodiments, a greater diameter D of the holes 562 may permit enhanced visibility through the lens 512.

In the illustrated embodiment, the cleaning ribbon 550 includes the segmenting elements 564 arranged between pairs of adjacent holes 562. The segmenting elements 564 are configured to inhibit the wicking of moisture by the cleaning ribbon 550 from contaminating the clean side 552 of the cleaning ribbon 550. In some embodiments, the segmenting elements 564 are separate components added to the cleaning ribbon 550, such as pieces of wax or another material that will conform to the fibers of the cleaning ribbon 550. In some embodiments, the segmenting elements 564 are formed by heating (e.g., melting) the cleaning ribbon 550 to agglomerate the fibers of the cleaning ribbon 550 together.

Figure 8A:
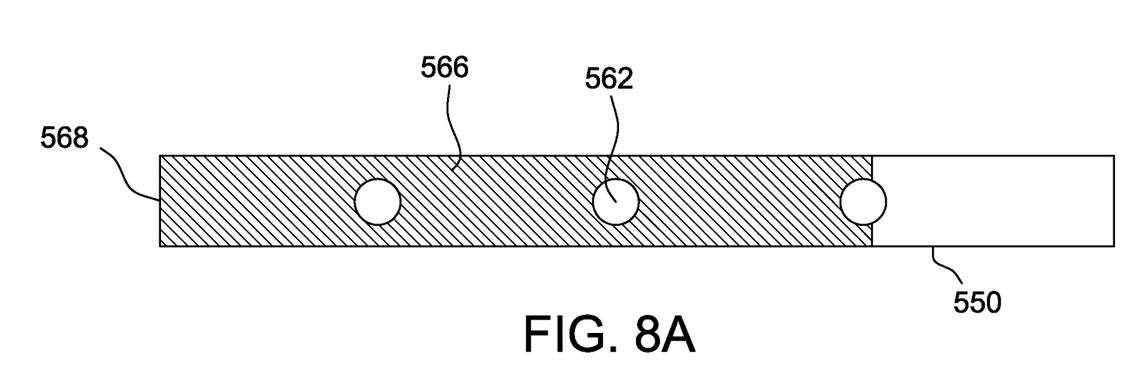
FIG. 8A is a top plan view of a cleaning ribbon without segmenting elements, suitable for use with the self-cleaning endoscope shown in FIG. 5.
Figure 8B:
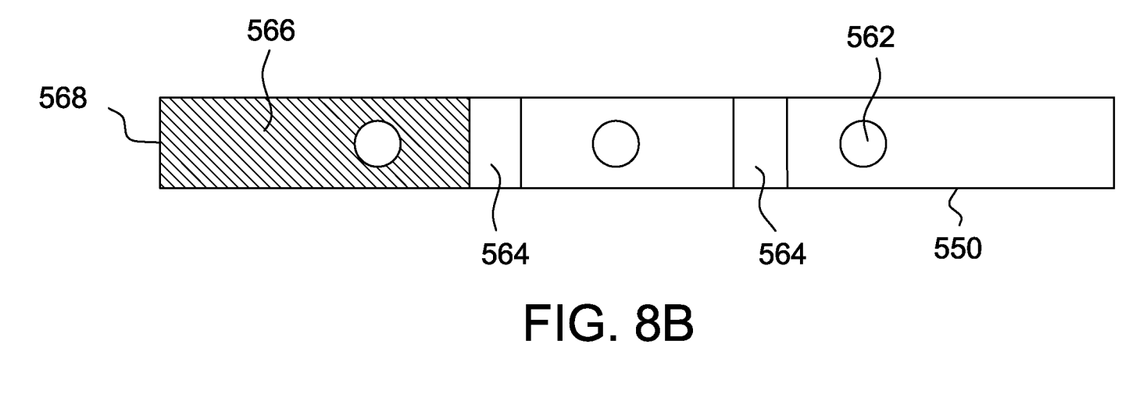
FIG. 8B is a top plan view of a cleaning ribbon with segmenting elements, suitable for use with the self-cleaning endoscope shown in FIG. 5.

FIG. 8A is a top plan view of a cleaning ribbon 550 without any segmenting elements 564, and FIG. 8B is a top plan view a cleaning ribbon 550' with a plurality of segmenting elements 564. The region of each cleaning ribbon 550, 550' that is hatched represents a contaminated portion 566, 566' of the cleaning ribbon 550, 550' (respectively) that is contaminated by wicked-up moisture, taken from a first end 568 of each cleaning ribbon 550, 550'. As illustrated in FIG. 8A, without the segmenting elements 564, moisture wicked by the cleaning ribbon 550 advances a great distance through the cleaning ribbon 550. In particular, if the illustrated cleaning ribbon 550 represents the clean side 552 of the cleaning ribbon 550, a great deal of the clean side 552 has been contaminated. Accordingly, an operator of the self-cleaning endoscope 500 would need to advance the cleaning ribbon 550 a greater distance and more often, which is both time-consuming and unnecessarily wasteful. In contrast, as illustrated in FIG. 8B, arranging the segmenting elements 564 between adjacent holes 562 inhibits moisture from being drawn into the cleaning ribbon 550' past the segmenting element 564. Accordingly, the clean side 552 of the cleaning ribbon 550' stays cleaner, and an operator need only advance the cleaning ribbon 550' to a subsequent hole 562.

The above-described self-cleaning endoscopes are configured for use within a viewing region within a patient's body without being drawing therefrom. One embodiment is designed to induce centrifugal force on debris collected on a lens protector, throwing the debris from the lens protector to maintain visibility from a lens therebelow. In this embodiment, a shaft extends from a motor to the lens protector and drives the rotation of the lens protector. Spacing the motor from a tip of the endoscope may increase maneuverability of the endoscope and/or improve handling comfort for an operator of the endoscope. Moreover, in some cases, the shaft doubles as a fluid conduit to spray a fluid onto the lens protector. The fluid can clear condensate and/or pick up smaller or lighter debris that can then be spun away. Providing a fluid source improves the usability of the self-cleaning endoscope. Designing the shaft to double as the fluid conduit permits the endoscope to keep a minimal, narrow profile. Another self-cleaning endoscope is designed as a retrofit to an existing, base endoscope. A ratchet mechanism draws a cleaning ribbon across the endoscope lens to clear away debris and draw up excess moisture. The cleaning ribbon has holes therein, such that the cleaning ribbon can be maintained in its cross-lens configuration and visibility therethrough is not sacrificed. Moreover, the cleaning ribbon includes segmenting elements to keep the clean side of the cleaning ribbon clean, decreasing waste and improving usability.

Exemplary embodiments of self-cleaning endoscopes and methods of using same are described above in detail. The self-cleaning endoscopes and methods of using same are not limited to the specific embodiments described herein, but rather, components of the catheter assembly and/or steps of the method may be utilized independently and separately from other components and/or steps described herein. For example, the cleaning assembly may also be used in combination with other systems and methods, such as angled and/or flexible base endoscopes, and is not limited to practice with only a straight, rigid endoscope as described herein. Rather, the exemplary embodiment can be implemented and utilized in connection with many other systems. For example, the cleaning assembly and/or the rotatable shaft may be employed with alternative optical devices, including borescopes (e.g., flexible, rigid, and/or video borescopes) and/or similar optical or gauging devices.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A self-cleaning endoscope comprising:
   a housing having a distal end and a proximal end opposite the distal end;
   a lens positioned at the distal end of the housing;
   a lens protector coupled to the distal end of the housing external to the lens;
   a shaft extending longitudinally through the housing, the shaft operatively coupled to the lens protector and configured to rotate the lens protector about an axis of rotation coaxial with the shaft, wherein the shaft is a hollow shaft that extends through the lens protector;
   a fluid source in fluid communication with the shaft and configured to drive fluid through the shaft to an external surface of the lens protector; and
   a motor at the proximal end of the housing, the motor operatively coupled to the shaft and configured to drive rotation of the shaft.
2. The self-cleaning endoscope of claim 1 further comprising a bearing interface between the fluid source and the shaft, the bearing interface configured to maintain the fluid source in a stationary position while enabling rotation of the shaft.

3. The self-cleaning endoscope of claim 1, wherein the fluid comprises saline.

4. The self-cleaning endoscope of claim 1 further comprising a trigger operatively coupled to the motor such that actuation of the trigger activates the motor to rotate the shaft.

5. The self-cleaning endoscope of claim 4, wherein the trigger is further operatively coupled to the fluid source such that actuation of the trigger activates the fluid source to drive fluid through the shaft.

6. The self-cleaning endoscope of claim 1 further comprising:
   a handle coupled to the proximal end of the housing; and
   a trigger located on the handle, wherein the trigger is operatively coupled to the motor such that actuation of the trigger activates the motor to rotate the shaft.

7. The self-cleaning endoscope of claim 1, wherein the shaft is coaxial with the housing.

8. The self-cleaning endoscope of claim 1, wherein the housing comprises:
   a tube that encloses the shaft; and
   a cap coupled to a distal end of the tube, wherein the lens protector is coupled to the cap, the cap defining a first opening that receives the shaft and a second opening that receives the lens.

9. The self-cleaning endoscope of claim 1 further comprising an optical component, wherein the optical component extends longitudinally through the housing and is coupled to the lens.

10. The self-cleaning endoscope of claim 9 further comprising a brace enclosed in the housing, wherein the brace is configured to maintain a position of the optical component within the housing.

11. The self-cleaning endoscope of claim 1, wherein the housing defines an opening at the distal end of the housing, the opening configured to receive a surgical tool therethrough.

12. A self-cleaning endoscope comprising:
   a housing having a distal end and a proximal end opposite the distal end;
   a lens positioned at the distal end of the housing;
   a lens protector coupled to the distal end of the housing external to the lens;
   a shaft extending longitudinally through the housing, the shaft operatively coupled to the lens protector and configured to rotate the lens protector about an axis of rotation coaxial with the shaft, wherein the shaft is a hollow shaft that extends through the lens protector;
   a fluid source in fluid communication with the shaft and configured to drive fluid through the shaft to an external surface of the lens protector;
   a motor at the proximal end of the housing, the motor operatively coupled to the shaft and configured to drive rotation of the shaft;
   a handle coupled to the proximal end of the housing; and
   a trigger located on the handle, wherein the trigger is operatively coupled to the motor and the fluid source such that actuation of the trigger activates the motor to rotate the shaft and the fluid source to drive fluid through the shaft.

13. The self-cleaning endoscope of claim 12, wherein the shaft is coaxial with the housing.

14. The self-cleaning endoscope of claim 12 further comprising a bearing interface between the fluid source and the shaft, the bearing interface configured to maintain the fluid source in a stationary position while enabling rotation of the shaft.

15. The self-cleaning endoscope of claim 12 further comprising a trigger operatively coupled to the motor such that actuation of the trigger activates the motor to rotate the shaft.

16. The self-cleaning endoscope of claim 15, wherein the trigger is further operatively coupled to the fluid source such that actuation of the trigger activates the fluid source to drive fluid through the shaft.

17. The self-cleaning endoscope of claim 12, wherein the housing defines an opening at the distal end of the housing, the opening configured to receive a surgical tool therethrough.

\* \* \* \* \*